US009360297B2

(12) United States Patent
Sugiyama et al.

(10) Patent No.: US 9,360,297 B2
(45) Date of Patent: Jun. 7, 2016

(54) OPTICAL COHERENCE TOMOGRAPHY DEVICE HAVING A PLURALITY OF CALIBRATION REFLECTING SURFACES (71) Applicant: Tomey Corporation, Nagoya-shi, Aichi-ken (JP)

(72) Inventors: Satoshi Sugiyama, Nagoya (JP); Yuji Nozawa, Nagoya (JP)

(73) Assignee: Tomey Corporation, Nagoya-Shi (JP)

( * ) Notice: Subject to any disclaimer, the term of this patent is extended or adjusted under 35 U.S.C. 154(b) by 0 days.

(21) Appl. No.: 14/267,283

(22) Filed: May 1, 2014

(65) Prior Publication Data

US 2014/0327918 A1 Nov. 6, 2014

(30) Foreign Application Priority Data

May 2, 2013 (JP) .................................. 2013-096752

(51) Int. Cl.
*G01B 9/02* (2006.01)
*A61B 3/10* (2006.01)
(52) U.S. Cl.
CPC ............ *G01B 9/02091* (2013.01); *A61B 3/102* (2013.01); *G01B 9/02072* (2013.04); *A61B 2560/0228* (2013.01)
(58) Field of Classification Search
CPC ........... G01B 9/02091; G01B 9/02072; G01B 9/02002; G01B 9/02004; G01B 9/02044; G01B 9/02083; G01B 9/0209; A61B 3/102; A61B 2560/0228; A61B 5/0066; A61B 5/0073; A61B 5/0084; A61B 5/6852; G01N 21/4795
See application file for complete search history.

(56) References Cited

U.S. PATENT DOCUMENTS 5,956,355 A    9/1999  Swanson et al.
5,994,690 A *  11/1999 Kulkarni et al. .............. 250/216
(Continued)

FOREIGN PATENT DOCUMENTS

EP    2 633 803 A1    9/2013
JP    2007-101365    4/2007
(Continued)

OTHER PUBLICATIONS

European Search Report for EP Application No. 14166839.2-1660; mailed Oct. 15, 2014; 11 pages.
(Continued)

*Primary Examiner* — Michael P Lapage
(74) *Attorney, Agent, or Firm* — Shumaker, Loop & Kendrick, LLP (57) ABSTRACT

Provided is an optical tomographic device including a measurement optical system that irradiates light from a light source to inside a subject and guides reflected light therefrom; a reference optical system that guides the light from the light source as reference light; a calibration optical system that irradiates a calibration reflecting surface with light from the light source, and guides the reflected light reflected by the calibration reflecting surface; a light-receiving element that receives the interfering light for measurement formed by synthesizing the reflected light guided by the measurement optical system and the reference light, and the interfering light for calibration formed by synthesizing the reflected light guided by the calibration optical system and the reference light; and an arithmetic logic unit that corrects the received interfering light for measurement by using an analysis result obtained by analyzing the received the interfering light for calibration.

2 Claims, 6 Drawing Sheets

(56) References Cited

U.S. PATENT DOCUMENTS

| | | | |
|---|---|---|---|
| 6,160,826 A * | 12/2000 | Swanson | A61B 1/00183 372/102 |
| 2005/0057756 A1 * | 3/2005 | Fang-Yen | G01B 9/02072 356/497 |
| 2006/0279742 A1 * | 12/2006 | Tearney et al. | 356/498 |
| 2007/0127033 A1 * | 6/2007 | Ueno | 356/497 |
| 2009/0261240 A1 | 10/2009 | Watanabe et al. | |
| 2011/0181890 A1 | 7/2011 | Hsu et al. | |
| 2011/0292395 A1 * | 12/2011 | Fercher et al. | 356/451 |
| 2013/0185023 A1 * | 7/2013 | Vakoc et al. | 702/189 |
| 2013/0222813 A1 | 8/2013 | Watanabe et al. | |
| 2014/0221827 A1 * | 8/2014 | Motaghiannezam et al. | 600/425 |
| 2014/0343411 A1 * | 11/2014 | O'Brien et al. | 600/425 |

FOREIGN PATENT DOCUMENTS

| | | |
|---|---|---|
| JP | 2010-014459 | 1/2010 |
| JP | 2011-196771 | 10/2011 |

OTHER PUBLICATIONS

Motaghiannezam, Reza et al.; "In Vivo Human Retinal and Choroidal Vasculature Visualization Using Differential Phase Contrast Swept Source Optical Coherence Tomography at 1060 NM"; Optical Coherence Tomography and Coherence Doman Optical Methods in Biomedicine XVI, Spie 1000, vol. 8213, No. 1, Jan. 30, 2012, pp. 1-7, 20th St., Bellingham, WA 98225-6705, U.S.A.

Vakoc, B. J. et al.; "Phase-Resolved Optical Frequency Domain Imaging"; Optics Express, OSA (Optical Society of America), vol. 13, No. 14, Jun. 11, 2005, pp. 5483-5493, Washington, DC, U.S.A.

* cited by examiner

OPTICAL COHERENCE TOMOGRAPHY DEVICE HAVING A PLURALITY OF CALIBRATION REFLECTING SURFACES

CROSS-REFERENCE TO RELATED APPLICATION

This application claims priority to Japanese Patent Application No. 2013-96752 filed on May 2, 2013, the contents of which are hereby incorporated by reference into the present application.

TECHNICAL FIELD

The present teachings relate to an optical coherence tomography.

DESCRIPTION OF RELATED ART

Tomographic devices for producing tomograms through the use of optical coherence are being developed (for example, an ophthalmic device for examining a subject's eye). Tomographic devices of this type include a Fourier-domain type using a wavelength sweeping light source (a so-called SS-OCT type). A tomographic device of the SS-OCT type can acquire data fast since a wavelength sweeping light source is used, but on the other hand there is a problem that the wavelength of light outputted from the wavelength sweeping light source does not linearly change with time. As a result, if an interference signal is sampled at regular time intervals, a coherence waveform acquired contains a frequency error. Therefore, techniques for solving the nonlinearity of the wavelength sweeping light source have been developed (for example, Japanese Patent Application Publication No. 2010-14459, Japanese Patent Application Publication No. 2011-196771).

In the technique of the Japanese Patent Application Publication No. 2010-14459, a calibration jig is attached to a tomographic device, and a reflecting surface of the calibration jig is irradiated with measuring light. Then, an interference signal acquired from interfering light of the measuring light reflected from the reflecting surface and reference light are sampled to prepare data for calibration. In the case where a tomogram of a subject is produced, an optical probe for measurement is attached to the tomographic device in place of the calibration jig, the subject is imaged by means of the optical probe, and the imaging result is corrected by the data for calibration.

On the other hand, in the technique of the Japanese Patent Application Publication No. 2011-196771, a sweep rate detection unit is provided to detect the sweep rate of the frequency of light outputted from a light source. The sweep rate detection unit is composed of interferometer with two mirrors and a detector. The light outputted from the light source is branched and inputted into the sweep rate detection unit. The light inputted into the sweep rate detection unit is split into two light beams. The split two light beams are caused to interfere with each other, and the interfering light is measured by the detector. From this signal, the wavelength sweep rate of the light source is detected, and correction of a coherent signal acquired from an optical system for measurement is performed.

SUMMARY

In the technique of the Japanese Patent Application Publication No. 2010-14459, in order to prepare the data for calibration, it is necessary to detach the optical probe for measurement from the tomographic device to attach the calibration jig to the tomographic device. Also, after the data for calibration is prepared, it is necessary to detach the calibration jig from the tomographic device to attach the optical probe for measurement to the tomographic device again. As a result, the data for calibration cannot easily be prepared. On the other hand, in the technique of the Japanese Patent Application Publication No. 2011-196771, in addition to an interference optical system for measuring (imaging) a subject (that is, a measurement optical system and a reference optical system), another interference optical system for detecting the wavelength sweep rate must be mounted. Since the two interference optical systems must be mounted on a single tomographic device, there is such a problem that the device configuration becomes complicated.

The specification of this application will disclose an optical tomographic device that has a simple device configuration and yet can easily prepare data for calibration.

A device for obtaining an optical tomographic image disclosed in this specification includes a light source, a measurement optical system, a reference optical system, a calibration optical system, and an arithmetic logic unit. The light source is configured to periodically scan a wavelength of light. The measurement optical system is configured to irradiate light from the light source into an inside of a subject and guide reflected light from the inside of the subject. The reference optical system is configured to guide the light from the light source as reference light. The calibration optical system is configured to irradiate at least one calibration reflecting surface with light from the light source branched from the measurement optical system or the reference optical system, and guide reflected light reflected by the calibration reflecting surface. The light-receiving element is configured to measure an interfering light for measurement of the reflected light guided by the measurement optical system and the reference light guided by the reference optical system and an interfering light for calibration of the reflected light guided by the calibration optical system and the reference light guided by the reference optical system. The arithmetic logic unit corrects an interference signal for measurement received by the light-receiving element by using an analysis result obtained from an interfering light for calibration received by the light-receiving element.

This tomographic device is provided with the calibration optical system for correcting the nonlinearity of a wavelength sweeping of the light source. This calibration optical system guides light branched from the measurement optical system or the reference optical system to the calibration reflecting surface, which is herein a reflecting surface for calibration, and guides reflected light from the calibration reflecting surface. Then, the interfering light for calibration is formed by the reflected light from the calibration optical system and reference light from the reference optical system, and the interfering light for calibration is received by the light-receiving element. The arithmetic logic unit prepares calibration data based on the interfering light for calibration. Since this tomographic device is provided with the calibration optical system having the calibration reflecting surface, it is not necessary to attach and detach a calibration jig to prepare calibration data. As a result, the calibration data can be easily prepared. In addition, the interfering light for calibration and the interfering light for measurement are synthesized and detected by the same light-receiving element. For this reason, the optical systems share one or more components therein for generating/detecting the interfering light for calibration and the interfering light for measurement. Therefore, complication of the device configuration can be suppressed.

DETAILED DESCRIPTION

In a tomographic device disclosed in the specification, at least one calibration reflecting surface in a calibration optical system may be fixed at a position where an optical path length from a light source is a preset length. According to such a configuration, since the optical path length of calibration reflected light becomes constant, the frequency of the interfering light for calibration also becomes substantially constant. As a result, a processing for preparing calibration data can be easily performed.

In the tomographic device disclosed in the specification, at least one calibration reflecting surface in a calibration optical system may be movable in an optical axis direction. According to such a configuration, when calibration data is prepared, the interfering light for calibration can be measured with substantially the same optical path length from the light source to the calibration reflecting surface as an optical path length from the light source to a subject. As a result, calibration data of an appropriate frequency corresponding to the position of a subject can be prepared. It should be noted that when an optical tomogram of the subject is produced, the calibration reflecting surface can be moved such that an optical path length to the calibration reflecting surface differs from an optical path length to the subject. As a result, there is no influence on the production of an optical tomogram of the subject.

Embodiment

Figure 1:
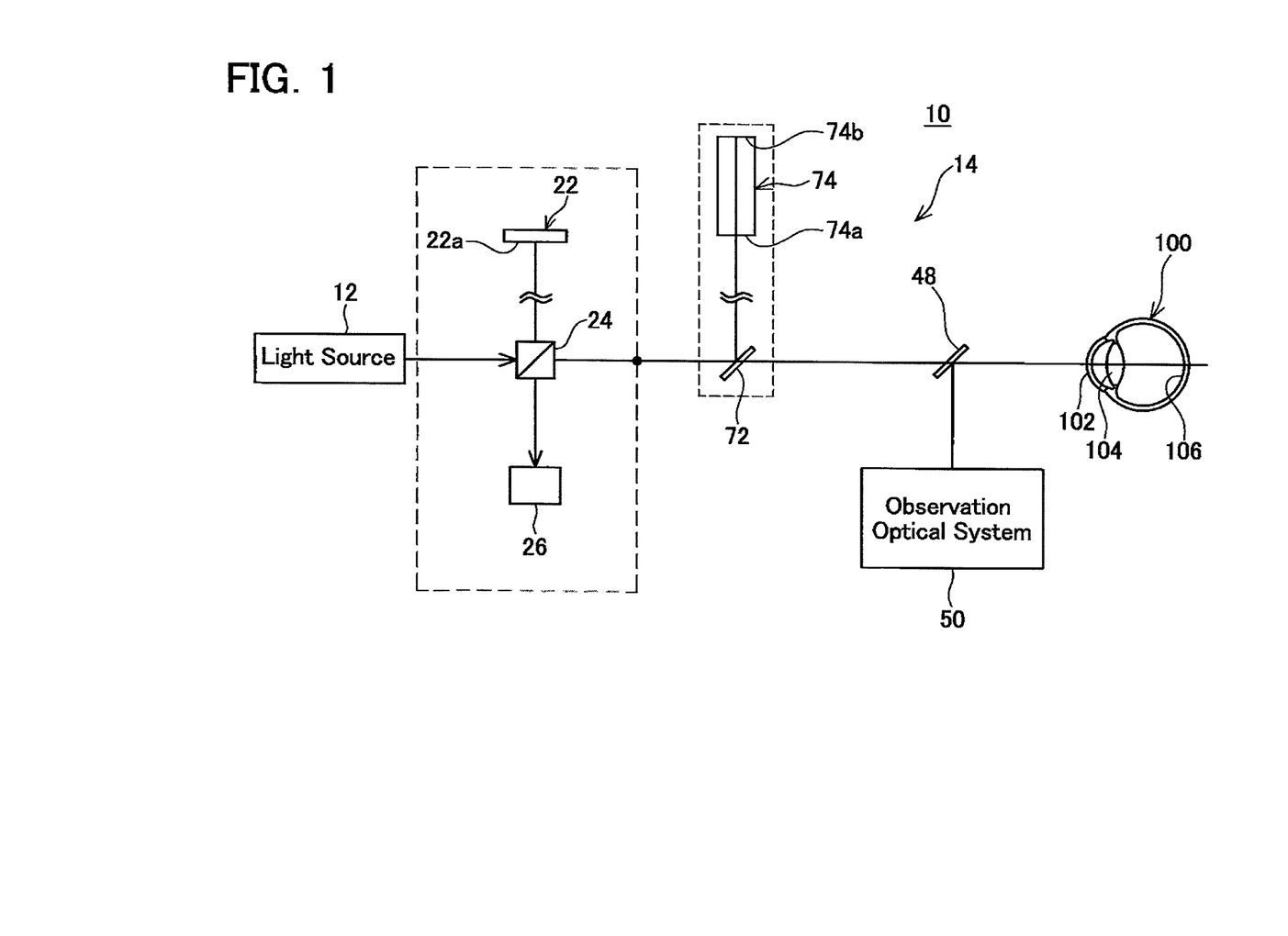
FIG. 1 is a schematic configuration diagram of an optical system of an ophthalmic device according to an embodiment.

As shown in FIG. 1, an ophthalmic device of the embodiment has a measuring unit 10 for examining a subject's eye 100. The measuring unit 10 has an interference optical system 14 for causing reflected light reflected from the subject's eye 100 and reference light to interfere with each other, an observation optical system 50 for observing an anterior eye part of the subject's eye 100, and an alignment optical system (not shown) for aligning the measuring unit 10 with the subject's eye 100 such that a predetermined positional relationship is made therebetween. As the alignment optical system, one used in a known ophthalmic device can be used, so the description of the details thereof is omitted.

The interference optical system 14 is composed of a light source 12, a measurement optical system (24, 72, 48) that irradiates light from the light source 12 into an inside of the subject's eye and guides reflected light therefrom, a reference optical system (24, 22) that irradiates a reference surface 22a with light from the light source 12 and guides reflected light therefrom, a calibration optical system (24, 72, 74) that irradiates reflecting surfaces (74a, 74b) with light from the light source 12 and guiding reflected light therefrom, and a light-receiving element 26 receiving the interfering light for measurement formed by synthesizing the reflected light guided by the measurement optical system and the reflected light guided by the reference optical system, and the interfering light for calibration formed by synthesizing the reflected light guided by the calibration optical system and the reflected light guided by the reference optical system.

The light source 12 is a wavelength sweeping light source, and is configured to change a wavelength (wavenumber) of outgoing light in a predetermined periodic cycle. That is, the ophthalmic device of the embodiment irradiates the subject's eye 100 with the light emitted by the light source 12 while changing (scanning) the wavelength. Then, by applying Fourier analysis to a signal acquired from interfering light of the reflected light from the subject's eye 100 and reference light, intensity distribution of light reflected from respective regions in a depth direction of the subject's eye 100 is acquired. Once the light intensity distribution in the depth direction of the subject's eye 100 is acquired, it becomes possible to locate the positions of the respective regions inside the subject's eye 100 (that is, a crystalline lens 104, a retina 106, and the like), as described below. It should be noted that it is preferable for the wavelength of the light emitted from the light source 12 to change linearly over time, but actually the wavelength has a small degree of nonlinearity. This nonlinearity also changes with aging of the light source 12. In order to correct this change at the right time, in the embodiment, calibration data for correcting the nonlinearity of wavelength sweep of the light source 12 can be prepared without any operation by a user. Since the calibration data is acquired regularly, the subject's eye 100 can be examined properly even if the ophthalmic device has aged.

The measurement optical system is composed of a beam splitter 24, a beam splitter 72, and a hot mirror 48. The subject's eye 100 is irradiated with light emitted from the light source 12 via the beam splitter 24, the beam splitter 72, and the hot mirror 48. The reflected light from the subject's eye 100 is guided to the light-receiving element 26 via the hot mirror 48, the beam splitter 72, and the beam splitter 24.

The reference optical system is composed of the beam splitter 24 and a reference mirror 22. Part of the light emitted from the light source 12 is reflected by the beam splitter 24, delivered to a reference surface 22a of the reference mirror 22, and reflected by the reference surface 22a of the reference mirror 22. The light reflected by the reference mirror 22 is guided to the light-receiving element 26 via the beam splitter 24. The reference mirror 22 is set to be movable. In the embodiment, the reference mirror 22 is moved before measurement is started, so that a measurement optical path length and a reference optical path length are caused to coincide with each other. It should be noted that in the case of a Fourier domain type using the wavelength sweeping light source 12, like the embodiment, the reference mirror 22 is not moved during the subsequent measurement.

The calibration optical system is composed of the beam splitter 24, the beam splitter 72, and an optical component 74. The light emitted from the light source 12 is delivered to the optical component 74 via the beam splitter 24 and the beam splitter 72. That is, the light emitted from the light source 12 is branched from the measurement optical system by the beam splitter 72, and the branched light is delivered to the optical component 74. The optical component 74 has a first reflecting surface 74a on one end and a second reflecting surface 74b on the other end. Therefore, part of light delivered to the optical component 74 is reflected by the first reflecting surface 74a, and the rest enters the optical component 74. Part of the light that has entered the optical component 74 is reflected by the second reflecting surface 74b, and the rest is delivered outside from the optical component 74. The light reflected by the first reflecting surface 74a and the light reflected by the second reflecting surface 74b are guided to the light-receiving element 26 via the beam splitter 72 and the beam splitter 24. It should be noted that, in the embodiment, the calibration data for correcting the nonlinearity of the wavelength of the light source 12 is prepared by using the reflected light from one reflecting surface (for example, the first reflecting surface 74a). In addition, as described below, the reflected lights from the first reflecting surface 74a and the second reflecting surface 74b are used to calibrate an eye axial length of the subject's eye 100 by taking advantage of the fact that a distance between the reflecting surfaces is known.

Here, in the calibration optical system of the embodiment, the optical component 74 is made movable in the optical axis direction. Specifically, the position in the optical axial direction of the optical component 74 can be adjusted by a second driving device 56 (shown in FIG. 2) driving a second positional adjustment mechanism 12 (shown in FIG. 2). Thereby, optical path lengths from the light source 12 to the respective reflecting surfaces 74a and 74b can be adjusted. For example, in the case of acquiring the calibration data for correcting the nonlinearity of the light source 12, the optical component 74 is positioned such that an optical path length from a zero point to the first reflecting surface 74a is substantially equal to a distance from the zero point to the cornea or retina of the subject's eye 100 (which is, however, not a subject's eye to be examined but a designed subject's eye). This makes it possible to acquire the calibration data close to a frequency range used to produce a tomogram of the subject's eye 100. On the other hand, when the tomogram of the subject's eye 100 is produced, the optical component 74 is positioned such that an optical path length from the zero point to the first reflecting surface 74a and an optical path length from the zero point to the second reflecting surface 74b are longer than a distance from the zero point to the retina of the subject's eye 100 (a subject's eye to be examined actually). This makes it possible to eliminate the influence of the optical component 74 on the production of a tomogram of the subject's eye 100. In this regard, the zero point means a point at which an optical path length of the reference optical system (reference optical path length) and an optical path length of an object optical system (object optical path length) are equal to each other (see FIG. 3). It should be noted that a difference between the optical path length from the zero point to the first reflecting surface 74a and the optical path length from the zero point to the second reflecting surface 74b depends on a length from the first reflecting surface 74a on one end of the optical component to the second reflecting surface 74b on the other end. As described later, a measured eye axial length can be calibrated by taking advantage of the fact that the distance between the reflecting surfaces is known, that is, the shape (length) of the optical component is known. Increase in shape precision of the optical component 74 allows the difference between the optical path lengths to be managed with high precision, which can result in enhancement of calibration precision.

It should be noted that an optical glass, for example, can be used for the optical component 74. By irradiating the optical glass with light from the light source 12, one end (entrance surface) of the optical glass can be functioned as a first reflecting surface, and the other end (exit surface) thereof as a second reflecting surface. As another example of the optical component 74, for example, an optical plastic or the like can be used.

The light-receiving element 26 detects the interfering light for measurement formed by synthesizing light guided by the reference optical system and light guided by the measurement optical system, and the interfering light for calibration formed by synthesizing the light guided by the reference optical system and light guided by the calibration optical system. As is obvious from the above description, the interfering light for calibration includes first interfering light for calibration formed by synthesizing light reflected by the first reflecting surface 74a (light guided by a first optical path portion) and light guided by the reference optical system, and second interfering light for calibration formed by synthesizing light reflected by the second reflecting surface 74b (light guided by a second optical path portion) and light guided by the reference optical system. Therefore, the light-receiving element 26 detects the interfering light for measurement, the first interfering light for calibration, and the second interfering light for calibration. A photodiode, for example, can be used as the light-receiving element 26. It should be noted, as described below, when the calibration data is acquired to correct the nonlinearity of the light source 12, the optical tomogram of the subject's eye 100 may be produced.

An observation optical system 50 irradiates the subject's eye 100 with observation light via the hot mirror 48, and produces reflected light from the subject's eye 100 (that is, reflected light of the delivered observation light). Here, the hot mirror 48 reflects light from the light source 12 of the interference optical system 12 while transmitting light from the light source of the observation optical system. As a result, in the ophthalmic device of the embodiment, measurement by the interference optical system and observation of the anterior eye part by the observation optical system 50 can be simultaneously performed. It should be noted that an observation optical system used in a known ophthalmic device can be used as the observation optical system 50, so the description of the detailed configuration thereof is omitted.

It should be noted that the ophthalmic device of the embodiment is provided with a first positional adjustment mechanism 16 (shown in FIG. 2) for adjusting the position of the measuring unit 10 relative to the subject's eye 100, and a first driving device 54 (shown in FIG. 2) driving the first positional adjustment mechanism 16. By driving the first driving device 54, the position of the measuring unit 10 relative to the subject's eye 100 is adjusted.

Figure 2:
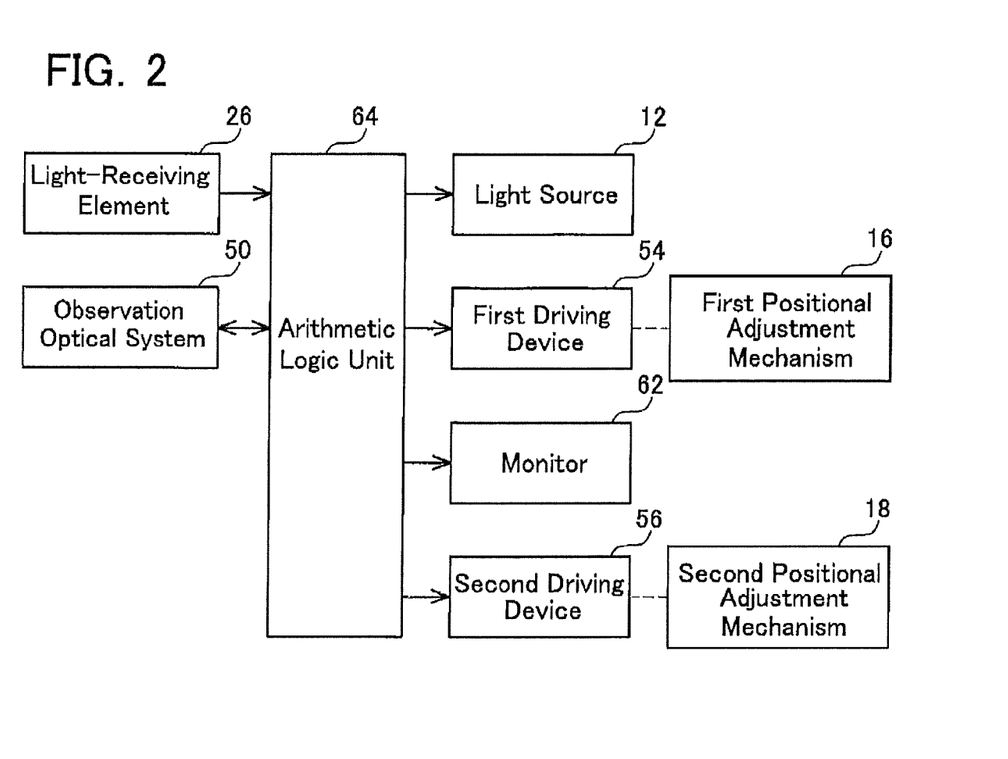
FIG. 2 is a block diagram of a control system of the ophthalmic device according to the embodiment.
Figure 3:
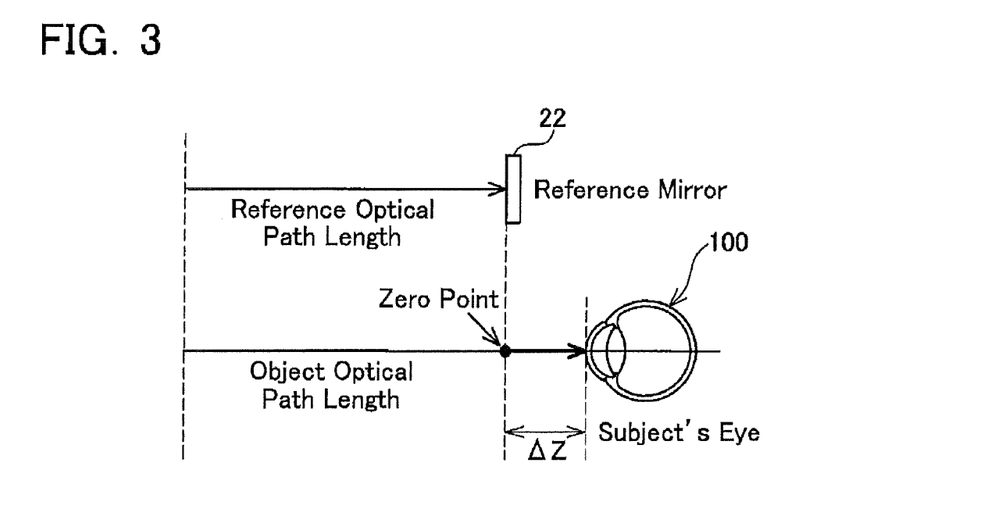
FIG. 3 is a diagram for illustrating a positional relationship between a zero point, a reference mirror, and a subject's eye.

Next, the configuration of a control system of the ophthalmic device of the embodiment will be described. As shown in FIG. 2, the ophthalmic device is controlled by an arithmetic logic unit 64. The arithmetic logic unit 64 is composed of a microcomputer (microprocessor) composed of CPU, ROM, RAM, and the like, and a gate array for fast operation. The arithmetic logic unit 64 is connected with the light source 12, the first driving device 54, a monitor 62, the second driving device 56, and the observation optical system 50. The arithmetic logic unit 64 controls on/off of the light source 12, controls the first driving device 54 to drive the first positional adjustment mechanism 16, controls the second driving device 56 to drive the second positional adjustment mechanism 18, and also controls the observation optical system 50 to display the anterior eye part captured by the observation optical system 50 on the monitor 62. The arithmetic logic unit 64 is also connected with the light-receiving element 26, and an interference signal corresponding to the intensity of the interfering light detected by the light-receiving element 26 (that is, the interfering light for measurement, the first interfering light for calibration, the second interfering light for calibration) is inputted to the arithmetic logic unit 64. The arithmetic logic unit 64 samples the interference signal from the light-receiving element 26 at preset constant time intervals, and uses the sampled data group to prepare the calibration data. In addition, by applying Fourier transform to a signal calibrated to a regular frequency interval by using the calibration data, the positions of respective regions of the subject's eye 100 (the anterior and posterior surfaces of the cornea 102, the anterior and posterior surfaces of the crystalline lens 104, and the surface of the retina 106) and the positions of the reflecting surfaces 74a and 74b of the optical component 74 are located, and these are used to compute the eye axial length of the subject's eye 100. It should be noted that the details of the processing performed by the arithmetic logic unit 64 is described later.

Figure 9:
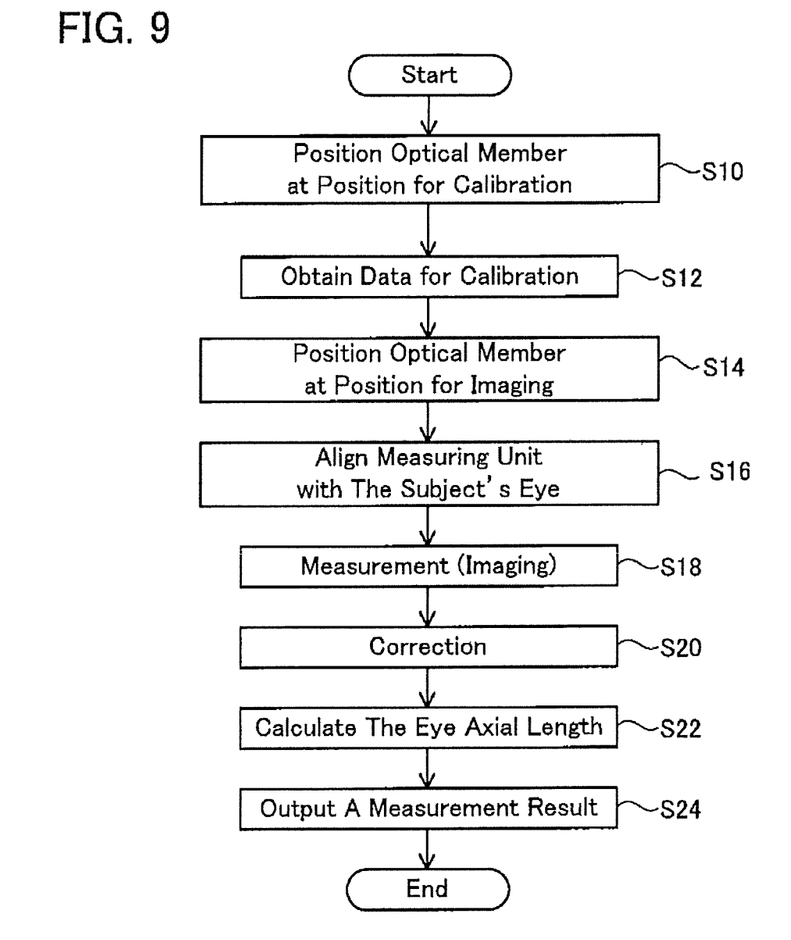
FIG. 9 is a flowchart showing an example of a processing procedure of the ophthalmic device according to the embodiment.

Next, the procedure of preparing the calibration data by using the ophthalmic device of the embodiment will be described. As shown in FIG. 9, in order to prepare the calibration data, first, the arithmetic logic unit 64 positions the optical component 74 at a position for preparing the calibration data (calibration position) (S10). That is, the arithmetic logic unit 64 makes the second driving device 56 drive the second positional adjustment mechanism 18 to position the optical component 74 at the calibration position. Once the optical component 74 is positioned at the calibration position, the optical path length from the zero point to the first reflecting surface 74a of the optical component 74 becomes substantially equal to the distance from the zero point to the cornea or retina of the subject's eye 100 (which is, however, not a subject's eye to be examined but a designed subject's eye).

Next, the arithmetic logic unit 64 takes in signal detected by the light-receiving element 26 while varying the frequency of light emitted from the light source 12 (S12). As already described, when the calibration data is prepared, the subject's eye 100 may be disposed in the measurement optical system. Here, description is made on the assumption that the subject's eye 100 is not disposed, but whether the subject's eye 100 is disposed or not has no influence on the procedure of preparing the calibration data. The light-receiving element 26 detects the first interfering light for calibration and the second interfering light for calibration, and inputs the interference signal based on the interfering light for calibrations to the arithmetic logic unit 64. The arithmetic logic unit 64 samples the interference signal inputted from the light-receiving element 26 at regular time intervals, and prepares the calibration data based on the sampled data. The processing of preparing the calibration data by the arithmetic logic unit 64 will be described in detail.

Figure 4:
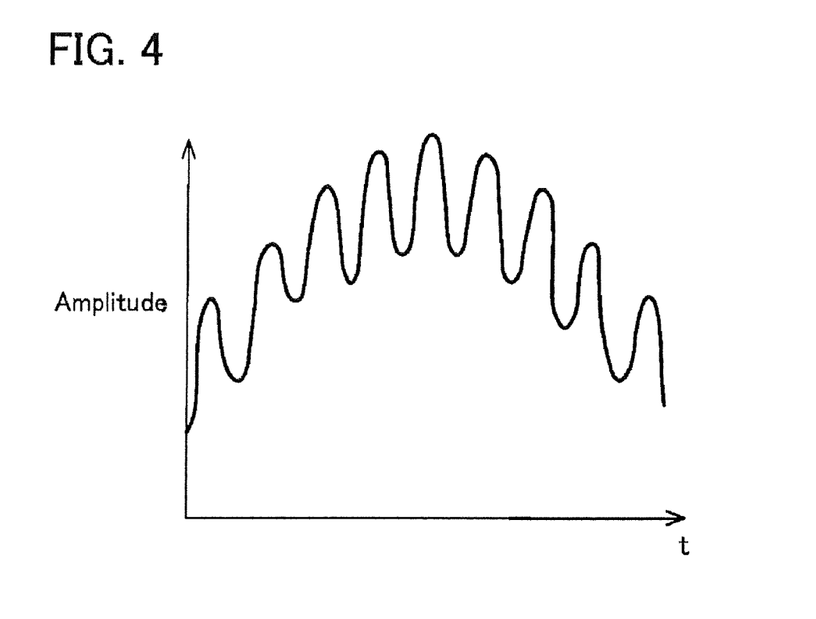
FIG. 4 is a diagram schematically showing the waveform of an interference signal of the interfering light for calibration.
Figure 5:
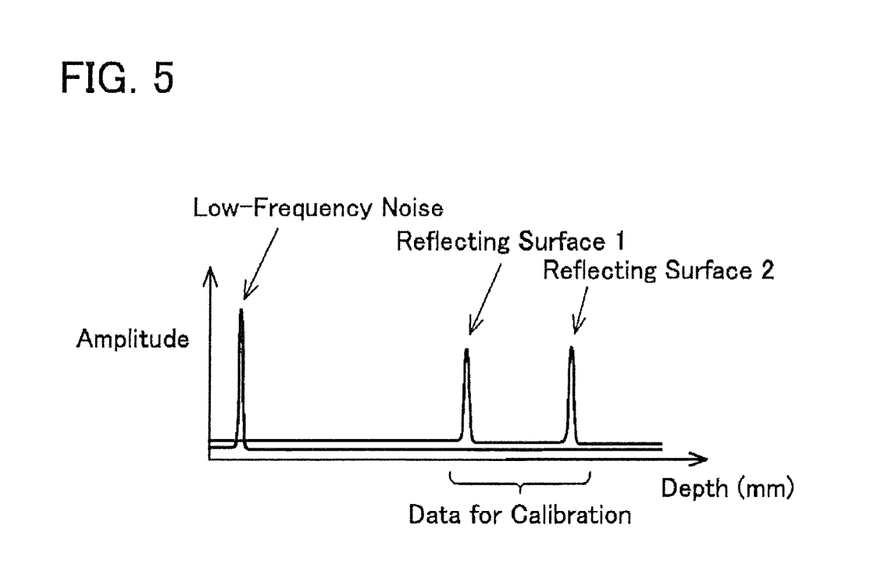
FIG. 5 is a diagram showing a waveform after Fourier transform of the waveform shown in FIG. 4.

The arithmetic logic unit 64 removes a frequency component unnecessary for preparation of the calibration data from the interference signal outputted from the light-receiving element 26, thereby shaping the interference signal. As shown in FIG. 4, the interference signal outputted from the light-receiving element 26 contains not only a signal component due to the interfering light for calibration but also a low-frequency beat component. In addition, though only a single the interfering light for calibration is used to prepare the calibration data, two interfering light for calibrations are contained in the embodiment. Therefore, the interference signal outputted from the light-receiving element 26 is decomposed into frequency components, as shown in FIG. 5, by Fourier transform. In an embodiment shown in FIG. 5, the interference signal is decomposed into a low-frequency component, a frequency component due to the first interfering light for calibration, and a frequency component due to the second interfering light for calibration. In the embodiment, only the frequency component due to the first interfering light for calibration is extracted, and the calibration data is prepared from the extracted first interfering light for calibration. It should be noted that, as described above, since the optical path length from the zero point to the first reflecting surface 74a is known, the frequency component of the first interfering light for calibration is also within a substantially constant range. Therefore, extraction of only the frequency component of the first interfering light for calibration can be easily performed.

Figure 6:
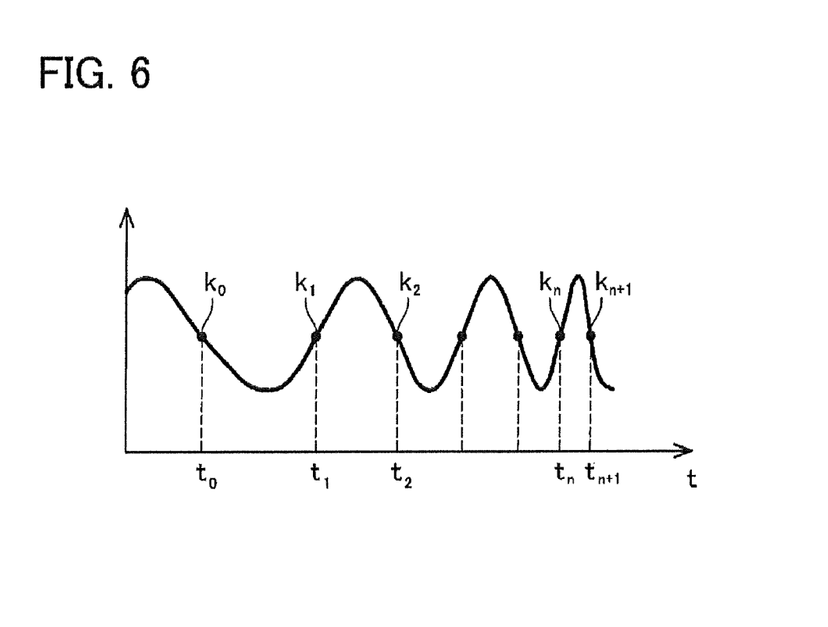
FIG. 6 is a diagram showing a waveform obtained by extracting a predetermined frequency domain from the waveform shown in FIG. 5 and applying inverse Fourier transform to the extracted waveform.
Figure 7:
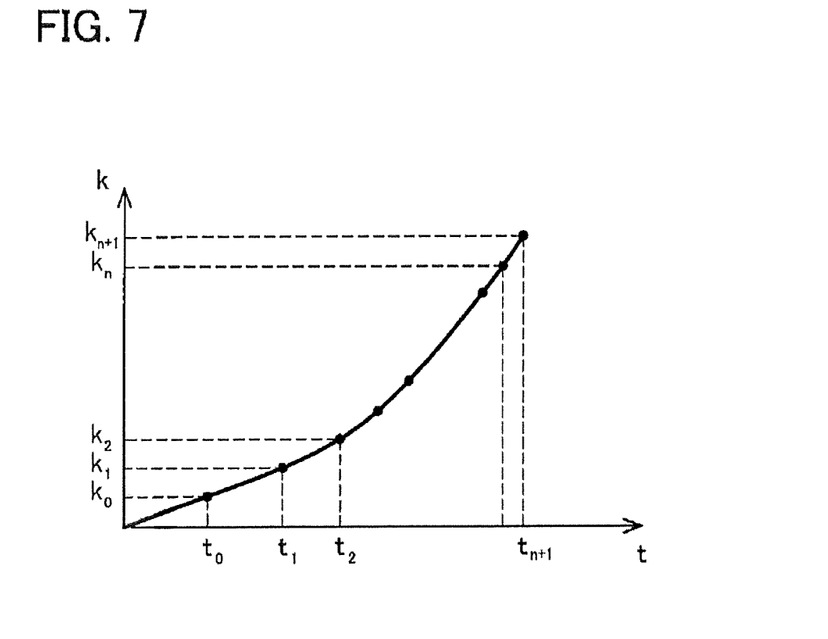
FIG. 7 is a diagram showing an example of calibration data.

When the extraction of only the frequency component of the first interfering light for calibration has been performed, then the arithmetic logic unit 64 applies inverse Fourier transform to the extracted frequency component to acquire such an interference signal containing only the first interfering light for calibration as shown in FIG. 6. Once the interference signal shown in FIG. 6 is generated, such calibration data as shown in FIG. 7 is prepared by a known method. The details of the processing of preparing the calibration data (FIG. 7) from the interference signal (FIG. 6) is disclosed, for example, in Japanese Patent Application Publication No. 2010-14459. From the calibration data, a relationship between frequency and time is acquired, so that interference signal (data group) acquired by sampling at regular time intervals can be converted into interference signal (data group) at regular frequency intervals.

When the calibration data has been prepared, then the arithmetic logic unit 64 positions the optical component 74 at a position for producing an optical tomogram of the subject's eye 100 (position for imaging) (S14). That is, the arithmetic logic unit 64 makes the second driving device 56 drive the second positional adjustment mechanism 18 to position the optical component 74 at the position for imaging. Once the optical component 74 is positioned at the position for imaging, the optical path length from the zero point to the first reflecting surface 74a and the optical path length from the zero point to the second reflecting surface 74b become longer than the distance from the zero point to the retina of the subject's eye 100.

Next, in order to examine the subject's eye 100, an examiner operates an operating member such as a joystick (not shown) to align the measuring unit 10 with the subject's eye 100 (S16). That is, the arithmetic logic unit 64 makes the first driving device 54 drive the positional adjustment mechanism 16 according to the examiner's operation of the operating member. Thus, a position in x and y directions (vertical and horizontal directions) and a position in z direction (advancing or retreating direction) of the measuring unit 10 relative to the subject's eye 100 are adjusted. In addition, the arithmetic logic unit 64 adjusts a focus adjustment mechanism (not shown) and a zero point adjustment mechanism (not shown) such that the position of a focal point of light which the light source 12 irradiates the subject's eye 100 with comes to a predetermined position of the subject's eye 100 (for example, the retina 106), and the position of a zero point where the object optical path length and the reference optical path length coincide with each other comes to a predetermined position relative to the subject's eye 100 (for example, a position slightly off the anterior surface of the cornea 102 toward the light source 12). It should be noted that the position of the zero point may be adjusted to a position slightly off the retina 106 toward the light source 12.

Figure 8:
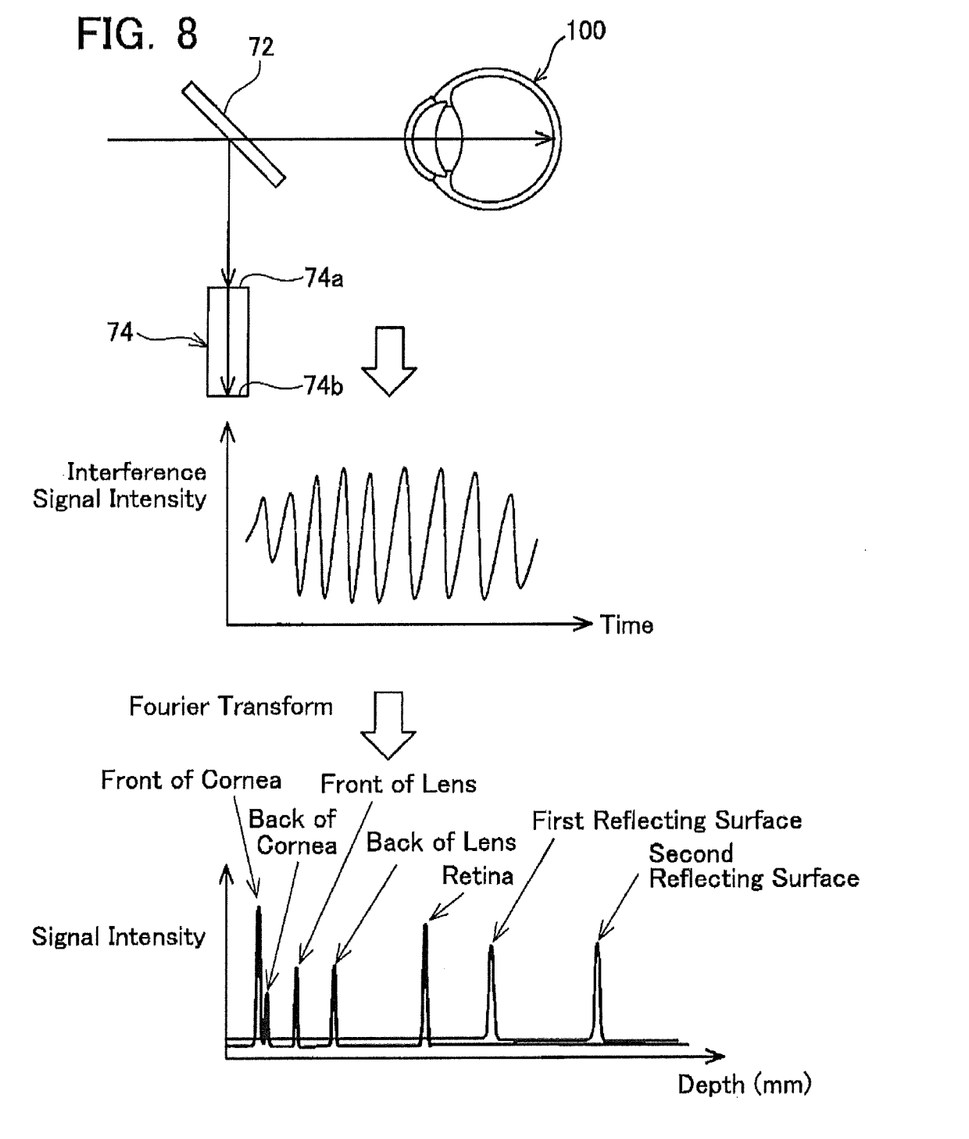
FIG. 8 is a diagram for explaining a procedure for processing an interference signal waveform acquired when an optical path length of a measurement optical system is scanned within a predetermined optical path length.

Next, the arithmetic logic unit 64 takes in a signal detected by the light-receiving element 26 while varying the frequency of light emitted from the light source 12 (S18). As described already, when an optical tomogram of the subject's eye 100 is produced, the interfering light received by the light-receiving element 26 contains lights reflected from respective regions in the depth direction of the subject's eye 100. That is, the interference signal outputted from the light-receiving element 26, as shown in FIG. 8, becomes a signal whose intensity varies with time, and this signal contains a signal due to a coherent wave formed by synthesizing respective reflected lights from respective portions of the subject's eye 100 (the anterior and posterior surfaces of the cornea 102, the anterior and posterior surfaces of the crystalline lens 104, the surface of the retina 106) and the first and second reflecting surfaces 74a and 74b, and the reference light, but since this interference signal is one sampled at a regular time interval, this interference signal contains a frequency error.

Next, the arithmetic logic unit 64 corrects the interference signal acquired at step S18 by the calibration data acquired at step S12 (S20). As described above, by using the calibration data, the interference signal (data group) acquired by sampling at regular time intervals can be converted into interference signal (data group) at regular frequency intervals. As a result, the interference signal acquired at step S18 (a group of data sampled at regular time intervals) are converted into a group of data at regular frequency intervals by the calibration data. It should be noted that correction of the interference signals by the calibration data can be performed in known various manners.

Next, the arithmetic logic unit 64 applies Fourier transform to the corrected interference signal, thereby locating the positions of respective regions of the subject's eye 100 (the anterior and posterior surfaces of the cornea 102, the anterior and posterior surfaces of the crystalline lens 104, the surface of the retina 106) and the positions of the first and second reflecting surfaces 74a and 74b and computing the eye axial length of the subject's eye 100 (a length from the surface of the cornea to the retina) (S22). Here, in the example, a position where the optical component 74 is disposed is adjusted relative to the zero point, so that, as shown in the bottom of FIG. 8, peaks indicating the positions of the respective regions of the subject's eye 100 and peaks indicating the positions of the first and second reflecting surfaces 74a and 74b do not overlap with each other. As a result, from the Fourier-transformed signal components, the positions of the respective regions of the subject's eye 100 and the positions of the first and second reflecting surfaces 74a and 74b can be located easily. Once the positions of the respective regions of the subject's eye 100 are located, the arithmetic logic unit 64 computes the eye axial length of the subject's eye 100 (a length from the surface of the cornea to the retina). Specifically, the arithmetic logic unit 64 first subtracts the position of the surface of the cornea of the subject's eye 100 from the position of the retina thereof, thereby computing the eye axial length based on the interfering light. Next, the arithmetic logic unit 64 subtracts the position of the first reflecting surface 74a from the position of the second reflecting surface 74b, thereby computing a length from the first reflecting surface 74a to the second reflecting surface 74b based on the interfering light. Here, the length from the first reflecting surface 74a to the second reflecting surface 74b corresponds to the length of the optical component 74, and the length of the optical component 74 is already known. Therefore, the eye axial length computed from the interfering light is corrected by means of the length of the optical component 74 (actual value) and the length of the optical component 74 acquired from the interfering light (measured value). Specifically, the computation is executed according to the following expression, that is, the eye axial length (corrected)=the eye axial length acquired from the interfering light×(the length of the optical component 74 (actual value)/the length of the optical component 74 acquired from the interfering light (measured value)).

The arithmetic logic unit 64 computes the eye axial length at step S22, and then displays the computed eye axial length on the monitor 62 (S24). The arithmetic logic unit 64 also displays on the monitor 62 an optical tomogram of the subject's eye 100 acquired from the interference signal corrected at step S20. In this manner, the arithmetic logic unit 64 completes the processing.

As is obvious from the above description, since the ophthalmic device according to the example is provided with the calibration optical system, the calibration data can be acquired without the use of a calibration jig. Therefore, the calibration data can be easily acquired. Further, the interfering light for calibration is generated by means of the reference light for imaging the subject's eye 100, and the interfering light for calibration is detected by the light-receiving element 26 for detecting the interfering light for measurement. Accordingly, the optical systems share one or more components therein, so that the device configuration can be simplified.

Furthermore, the calibration optical system is branched from the measurement optical system, the calibration optical system can be disposed in the vicinity of the subject's eye 100. This makes it possible to reduce the influence of an error factor of the optical system (for example, dispersion of optical fibers). As a result, precise calibration data can be acquired, so that precise imaging and measurement can be performed.

It should be noted that in the example, two reflecting surfaces 74a, 74b are provided in the calibration optical system. This also makes it possible to verify the calibration data from the optical path difference between the two reflecting surfaces 74a and 74b. Specifically, at above-described step S22, the positions of respective regions of the subject's eye 100 and the first reflecting surface 74a and the second reflecting surface 74b are located from the interference signal corrected by means of the calibration data. Then, from a difference (for example, a difference value) between a distance from the first reflecting surface 74a to the second reflecting surface 74b acquired from the interference signal and an actual length of the optical component 74 (a distance from the first reflecting surface 74a to the second reflecting surface 74b), the accuracy (precision) of the calibration data is evaluated. If the accuracy of the calibration data falls below a preset value, the fact that the precision of the calibration data has lowered is displayed on the monitor 62. This enables a user to know the necessity of preparation of the calibration data and perform the operation of preparing the calibration data. Further, in the embodiment, since a physical operation for acquiring the interference signal for calibration (attachment and detachment of a probe, or the like) is not required, if the accuracy of the calibration data has fallen below a preset value, it is also possible to reproduce the calibration data in a totally automatic manner. Therefore, it is possible to prevent the ophthalmic device 10 from continuing to be used with the precision of the calibration data lowered because of aging or the like of the ophthalmic device 10.

Specific embodiment of the present teachings is described above, but this merely illustrates some representative possibilities for utilizing the invention and does not restrict the claims thereof. The subject matter set forth in the claims includes variations and modifications of the specific embodiments set forth above.

For example, in the embodiment described above, the optical component 74 of the calibration optical system is so configured as to be movable, but such a configuration is not a restriction of the present invention. For example, the optical component 74 of the calibration optical system can also be immovably fixed. Immovable fixation of the optical component 74 makes the mechanisms 56 and 18 for moving the optical component 74 unnecessary. In addition, since the frequency of the interfering light for calibration detected by the light-receiving element 26 becomes constant, the processing of extracting the interfering light for calibration described above can be easily performed.

Additionally, in the embodiment described above, the ophthalmic device which mainly performs measurement of an eye axial length that is one-dimensional tomogram is described by way of example, but the technique disclosed in this text is applicable to an ophthalmic device that acquires a two-dimensional tomogram composed of a plurality of one-dimensional tomograms or even a three-dimensional tomogram composed of a plurality of two-dimensional tomograms. That is, the two-dimensional tomogram or the three-dimensional tomogram are both composed of a plurality of one-dimensional tomograms, so that by applying the calibration technique disclosed in this text to each of the plurality of one-dimensional tomograms constituting the two-dimensional tomogram or the three-dimensional tomogram, a more precise two-dimensional tomogram and/or three-dimensional tomogram can be acquired.

Additionally, in the embodiment described above, two reflecting surfaces 74a and 74b are provided in the calibration optical system, but one or more than two reflecting surfaces may be provided in the calibration optical system. That is, as long as at least one reflecting surface is provided in the calibration optical system, an interfering light for calibration can be acquired, so that the calibration data can be prepared from the interfering light for calibration.

If two or more reflecting surfaces are provided in the calibration optical system, like the embodiment described above, by acquiring an interference signal once, calibration of the nonlinearity of wavelength sweep of a light source and correction of measured values (an eye axial length or a plurality of one-dimensional tomograms in a two-dimensional tomogram or a three-dimensional tomogram) can also be simultaneously performed.

Additionally, in the embodiment described above, the subject's eye 100 is not disposed in the measurement optical system when the calibration data is acquired, but the arithmetic logic unit 64 extracts only a frequency component of the first interfering light for calibration from the interference signal outputted from the light-receiving element 64. Therefore, in the ophthalmic device of the embodiment described above, the calibration data can be prepared even under the condition that the subject's eye 100 is disposed in the measurement optical system. For this reason, in the case of measuring the subject's eye 100, the calibration data may be prepared for each performance of wavelength sweep.

Additionally, in the embodiment described above, the calibration optical system is branched from the measurement optical system, but the calibration optical system may be branched from the reference optical system. Further, the embodiment described above is an ophthalmic device for examining the human eye, but the technique disclosed in this text is also applicable to an optical tomographic device other than an ophthalmic device.

What is claimed is:

1. An optical tomographic device comprising:
a light source configured to periodically sweep a wavelength of light;
a measurement optical system configured to irradiate light from the light source into an inside of a human eye and guide reflected light from the inside of the human eye;
a reference optical system configured to guide the light from the light source as reference light;
a calibration optical system configured to irradiate an optical component comprising first and second reflecting surfaces positioned at opposite ends of the optical component with light from the light source branched from the measurement optical system or the reference optical system such that part of the light is reflected by the first reflecting surface while a remaining part of the light enters the optical component and a portion of the remaining part of light is reflected by the second reflecting surface;
a light-receiving element configured to receive a first interfering light for measurement comprised of the reflected light guided by the measurement optical system and the reference light guided by the reference optical system, and a second interfering light for calibration of the reflected light guided by the calibration optical system and the reference light guided by the reference optical system; and
an arithmetic logic unit configured to prepare calibration data for correcting a nonlinearity of the wavelength of the light source by analyzing the second interfering light for calibration received by the light-receiving element, when the optical component is positioned by a driving device such that an optical path length from a zero point to the first reflecting surface is substantially equal to a distance from the zero point to the cornea or retina of a designed human eye, the arithmetic logic unit then drives the optical component via the driving device such that an optical path length from the zero point to the first and second reflecting surfaces are longer than the distance from the zero point to the retina of the human eye, wherein the zero point refers to a point at which an optical path length of the reference optical system and an optical path length of the object optical system are equal to each other;
the arithmetic logic unit further calculates a corrected eye axial length with the following equation:

eye axial length(corrected)=(an eye axial length acquired from the first and second interfering light×the length of the optical component (actual value))/(the length of the optical component acquired from the first and second interfering light (measured value)).

2. The optical tomographic device according to claim 1, wherein at least one reflecting surface of the optical component is fixed at a position where an optical path length from the light source becomes a preset length.

* * * * *